United States Patent [19]
Copeland et al.

[11] 4,198,523
[45] Apr. 15, 1980

[54] SALT OF P-HYDROXYMANDELATE

[75] Inventors: Robert J. Copeland; Philip N. Edwards, both of Macclesfield, England

[73] Assignee: Imperial Chemical Industries Limited, London, England

[21] Appl. No.: 908,465

[22] Filed: May 22, 1978

[51] Int. Cl.$^2$ .......................................... C07C 65/135
[52] U.S. Cl. .................................................. 562/470
[58] Field of Search ........................................ 562/470

[56] References Cited
FOREIGN PATENT DOCUMENTS 1377243 12/1974 United Kingdom .................... 562/470

OTHER PUBLICATIONS

Chem. Abstracts, 38282g, vol. 67, 1967.
Chem. Abstracts, 37014n, vol. 68, 1968.

*Primary Examiner*—Paul J. Killos
*Attorney, Agent, or Firm*—Cushman, Darby & Cushman

[57] ABSTRACT

Solid sodium or potassium p-hydroxymandelate monohydrate and a process for isolating it from a known reaction mixture of phenol, glyoxylic acid and sodium or potassium hydroxide. The product is a useful intermediate for the preparation of the β-adrenergic blocking agent atenolol.

3 Claims, No Drawings

SALT OF P-HYDROXYMANDELATE

This invention relates to a novel salt and in particular it relates to an alkali metal salt of p-hydroxymandelic acid, which has the formula:

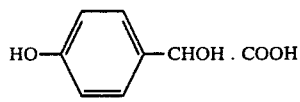

The preparation of p-hydroxymandelic acid has been described by a number of routes. For example, it has been obtained by the reaction of phenol with chloral, followed by the hydrolysis of the trichloromethyl group to the carboxylic acid group (Austrian specification No. 141,159; Chemical Abstracts, 1935, 29, 4021); or by the hydrolysis of p-hydroxybenzaldehyde cyanohydrin (Journal of the American Chemical Society 1936, 58, 1292); or by the diazotisation of p-aminomandelic acid (Il Farmaco, Edizione Scientifica, 1955, 10. 563); or by the reaction of phenol with glyoxylic acid (United Kingdom specification No. 1,377,243). In many of these preparations sodium hydroxide has been used as a reagent and therefore sodium p-hydroxymandelate has been present in solution, but there is no disclosure of this salt in solid form.

We have now found, and herein lies our invention, that a solid form of an alkali metal p-hydroxymandelate may conveniently be obtained in good yield and pure form, from the reaction of phenol with glyoxylic acid. Sodium p-hydroxymandelate in particular is a valuable intermediate for the preparation of p-hydroxyphenylacetamide, which is of use for the manufacture of the $\beta$-adrenergic blocking agent atenolol, as described in co-pending U.S. applications Ser. No. 908,463, now U.S. Pat. No. 4,154,757 and Ser. No. 908,466, filed May 22, 1978.

According to the invention there is provided solid sodium or potassium p-hydroxymandelate monohydrate.

According to a further feature of the invention there is provided a process for the manufacture of solid sodium or potassium p-hydroxymandelate monohydrate which comprises reacting by known means phenol with glyoxylic acid in the presence of, respectively, sodium or potassium hydroxide, followed by adjustment of the pH of the solution to between 5 and 6 and salting out of the desired sodium or potassium salt with respectively, a sodium or potassium salt of a simple acid.

The known process is preferably carried out at a temperature of between 20° and 60° C., preferably between 30° and 40° C., and preferably an excess of phenol of 50 to 100% w/w should be used.

A suitable sodium or potassium salt of a simple acid is, for example, a chloride, sulphate, formate or acetate. The chloride salt is preferred.

The desired sodium or potassium salt may be purified by washing with a saturated aqueous solution of, respectively, sodium or potassium chloride, and then with acetone to remove the excess of phenol.

Organic by-products of the reaction of phenol with glyoxylic acid do not form an insoluble sodium or potassium salt and are therefore removed in the mother liquors.

The invention is illustrated but not limited by the following Examples:

EXAMPLE 1

A mixture of phenol (368 g.), ice-water (400 g.) and aqueous 68% w/w sodium hydroxide solution (160 ml.) is added to a mixture of aqueous 50% w/w glyoxylic acid solution (356 g.), ice chips (800 g.) and aqueous 68% w/w sodium hydroxide solution (135 ml.) under an atmosphere of nitrogen, and the mixture is then heated at a temperature of 30°–35° C. for 18 hours. The mixture is acidified to pH 6 with concentrated aqueous hydrochloric acid (235 ml.) and then stirred and heated at 75°–80° C. Sodium chloride is added until the solution is nearly saturated, the phenol which separates out is removed and the aqueous solution is cooled in ice and then filtered. The solid product is washed with saturated aqueous sodium chloride solution and then with acetone and is then dried at 80° C. There is thus obtained sodium p-hydroxymandelate monohydrate, 381 g., 76% yield based on the glyoxylic acid used. The solid product also contains some sodium chloride, estimated by silver nitrate titration to be 45 g.

EXAMPLE 2

Aqueous sodium hydroxide solution (295 ml., 68% w/w is added slowly to a stirred mixture of phenol (368 g.), aqueous glyoxylic acid solution (356 g., 50% w/w) and water (100 ml.) which is maintained below 20° C. by external cooling. After the addition is complete the stirred mixture is heated at 35° C. for 5 hours and then acidified to pH 6 with concentrated aqueous hydrochloric acid (235 ml.). Solid sodium chloride is added until the hot solution (the temperature reaches 70° C. during acidification) is almost saturated, and the mixture is cooled to 20° C. and filtered. The solid residue is washed with saturated aqueous sodium chloride solution and then with acetone, and is then dried at 60° C. There is thus obtained sodium p-hydroxymandelate monohydrate, yield 63% based on the glyoxylic acid used, contaminated with solid sodium chloride.

EXAMPLE 3

A solution of potassium hydroxide (145.6 g.) in water (120 ml.) is added during one hour to a stirred mixture of phenol (184 g.), water (700 ml.) and 50% aqueous glyoxylic acid (178 g.), the temperature being maintained below 15° C. during the addition. The reaction temperature is then raised to 35° C. and the mixture is stirred at this temperature for 8 hours and then cooled. Concentrated aqueous hydrochloric acid is added until the pH of the mixture is 6, and then potassium chloride (300 g.) is added and the mixture is stirred for 2 hours and then filtered. The solid residue is washed with saturated aqueous potassium chloride solution (200 ml.) and then with acetone (250 ml.) and is then dried. There is thus obtained solid potassium p-phydroxymandelate monohydrate (26 g.) contaminated with solid potassium chloride.

What we claim is:

1. Solid purified sodium or potassium p-hydroxymandelate monohydrate, said monohydrate being free from organic impurities.

2. Solid purified sodium p-hydroxymandelate monohydrate according to claim 1, said monohydrate being free from organic impurities.

3. The product of claim 2 containing a small amount of sodium chloride.

* * * * *